US00PP37567P2

(12) United States Plant Patent
Byrne et al.

(10) Patent No.: US PP37,567 P2
(45) Date of Patent: Aug. 11, 2026

(54) PEACH TREE NAMED 'TRH3C114W'

(50) Latin Name: *Prunus persica*
Varietal Denomination: TRH3C114W

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,169

(22) Filed: Sep. 22, 2025

(51) Int. Cl.
*A01H 5/08* (2018.01)

(52) U.S. Cl.
USPC ..... Plt./194

(58) Field of Classification Search
USPC ..... Plt./194
CPC ..... A01H 6/7463; A01H 5/08
See application file for complete search history.

(56) References Cited

U.S. PATENT DOCUMENTS

PP14,627 P3 3/2004 Byrne et al.
PP14,629 P3 3/2004 Byrne et al.
PP26,119 P3 11/2015 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Byrne and Anderson, 2013. White Delight peach series: Four medium-chill, subacid, white-fleshed peaches. HortScience 48(8):1056-1058.

*Primary Examiner* — Keith O. Robinson
(74) *Attorney, Agent, or Firm* — Dentons US LLP

(57) ABSTRACT

Disclosed is a new variety of *Prunus persica* named 'TRH3C114W'. This new variety, which requires approximately 400 chilling units of dormancy, is a peach tree of early maturity, which produces acid-sweet, firm, clingstone to semi freestone, white-fleshed peach with a 70-95% dark pink to maroon blush over a light-yellow ground color that is suitable for the fresh market.

5 Drawing Sheets

Latin name of the genus and species of the plant claimed: *Prunus persica.*

Variety denomination: 'TRH3C114W'.

BACKGROUND OF THE INVENTION

This invention relates to a peach tree and, more specifically, to a peach tree referred to as a variety of *Prunus persica* named 'TRH3C114W', which requires approximately 400 chilling units of dormancy, matures in the early season and produces a firm clingstone to semi-freestone, white-fleshed, acid-sweet peach with a 70-95% dark pink to maroon blush over a light yellow ground color. The present peach tree was the result of an ongoing Stone Fruit Breeding Program in College Station, Brazos County, Texas. To this end, controlled crosses are made each year to produce seedling populations from which improved progenies are evaluated and selected. The seedling 'TRH3C114W' was derived from a cross between a medium-chill, white-flesh, subacid, peach 'White Delight Two' (Byrne and Anderson, 2013. White Delight peach series: Four medium-chill, subacid, white-fleshed peaches. HortScience 48 (8):1056-1058, not patented) and a low-chill acid-sweet, yellow-fleshed peach, 'TexFirst' (patented, U.S. Plant Pat. No. 26, 119P3, 24 Nov. 2015). Resulting seed from the cross between 'White Delight Two' and 'TexFirst' were planted in 2011 in an experimental plot in Floresville, TX. 'TRH3C114W' was marked for subsequent observation in 2013 and noted as having exceptional characteristics.

'TRH3C114W' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2023), Somerville (2016-2021) and Fairfield (2015-2020), Texas. This evaluation clearly demonstrated that the re-propagated trees were true to the characteristics of the original seedling in all observable aspects.

SUMMARY OF THE INVENTION

The 'TRH3C114W' peach is characterized by producing clingstone to semi-freestone, white-fleshed fruit that ripens in the early season and produces a firm, fruit with a 70-95% dark pink to maroon blush over a light-yellow ground color. In this regard, the present variety of peach tree bears fruit that ripen for commercial harvesting and shipment in mid-to late May, when the fruit is grown in the medium chill zone of Texas. 'TRH3C114W' blooms 2 weeks before its female parent 'White Delight Two' (not patented) and ~ 11 days after its pollen parent 'TexFirst' (patented). It ripens ~8 days before its female parent and ~4 weeks after its pollen parent. 'TRH3C114W' differs from its white-fleshed, subacid, peach female parent as it has acid flesh and differs from its yellow-fleshed, acid-sweet pollen parent as it is a white-flesh peach. This new acid-sweet, white-fleshed peach exhibits potential to be commercialized in regions that have chilling requirements that are relatively low.

The commercial cultivar 'White Zest One' (not patented, U.S. app. Publication No. 2016/0205836 P1, abandoned) differs from 'TRH3114W' as it requires 150 more chilling hours to break dormancy, blooms ~10 days later, and ripens a week later than does 'TRH3C114W'. The commercial cultivar 'White Delight Two' (not patented; U.S. app. Publication No. 2016/0205832 P1, abandoned) differs from 'TRH3C114W' in that it has subacid rather than acid flesh, requires 150 more chilling hours to break dormancy, blooms 2 weeks later, ripens ~ 9 days later than does 'TRH3C114W'. 'TRH3C114W' has the same parentage as 'TRH2B102LW' (U.S. Ser. No. 19/336,385), 'TRH2C108W' (U.S. Ser. No. 19/336,380) and 'TRH2E122W' (U.S. Ser. No. 19/295, 148). 'TRH3C114W' differs from the selection 'TRH2E122W' as it has less anthocyanin accumulation in the flesh (10-25% vs. 70-80%), has reniform leaf glands rather than globose leaf glands and ripens about two weeks earlier than does 'TRH2E122W'. 'TRH2B102LW' differs from 'TRH3C114W' as it has a subacid flavor, requires more chilling, blooms about 2 weeks later, ripens about one week earlier and has a shorter fruit development period than does 'TRH3C114W'. 'TRH2C108W' differs from 'TRH3C114W' as it ripens about one week earlier than does 'TRH3C114W'.

BRIEF DESCRIPTION OF THE DRAWINGS

This new variety of peach tree is illustrated by the accompanying photographs of five-year old plants grown in Fairfield, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
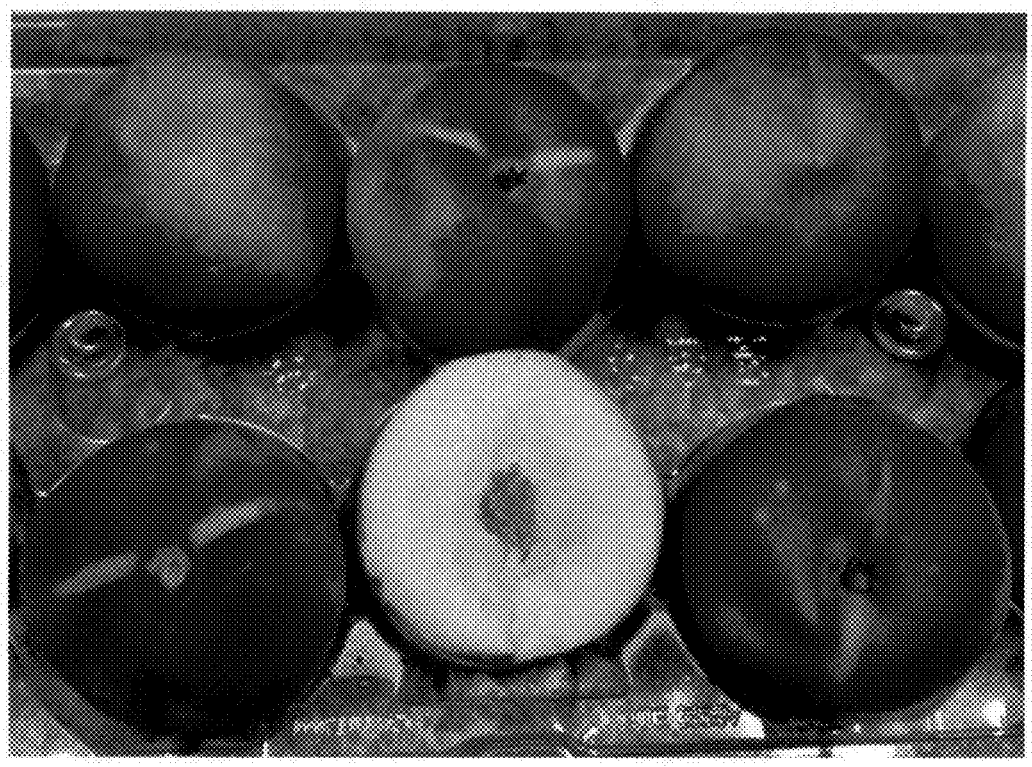
FIG. 1. Fruit of 'TRH3C114W' produced in Fairfield, Texas showing external and internal coloration.
Figure 2:
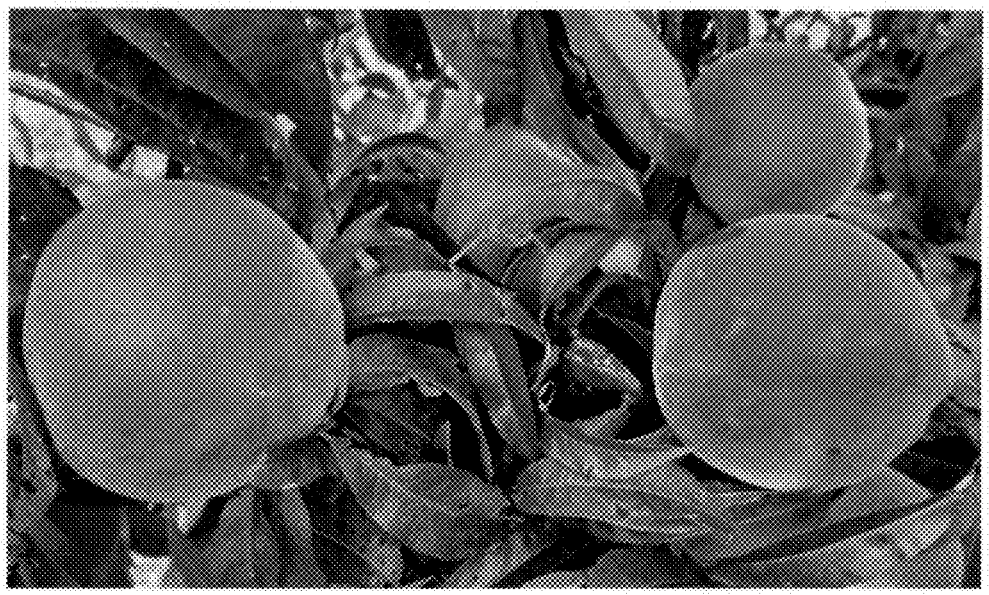
FIG. 2. 'TRH3C114W' fruit produced in Fairfield, Texas showing shape and external coloration.
Figure 3:
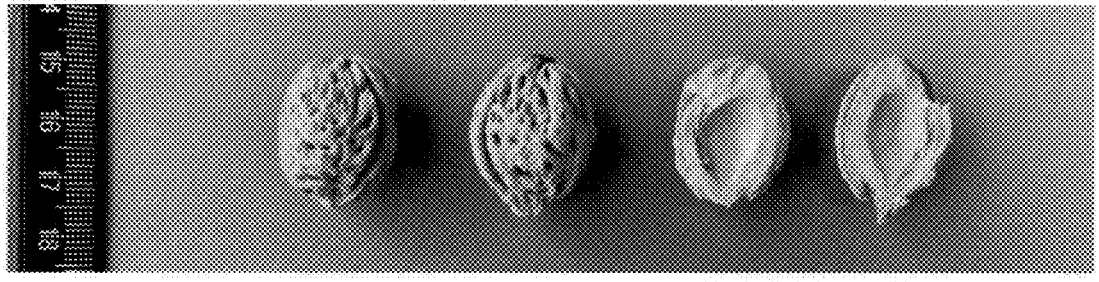
FIG. 3. Photograph of the endocarps of 'TRH3C114W' peach. The ruler is in centimeters.
Figure 4:
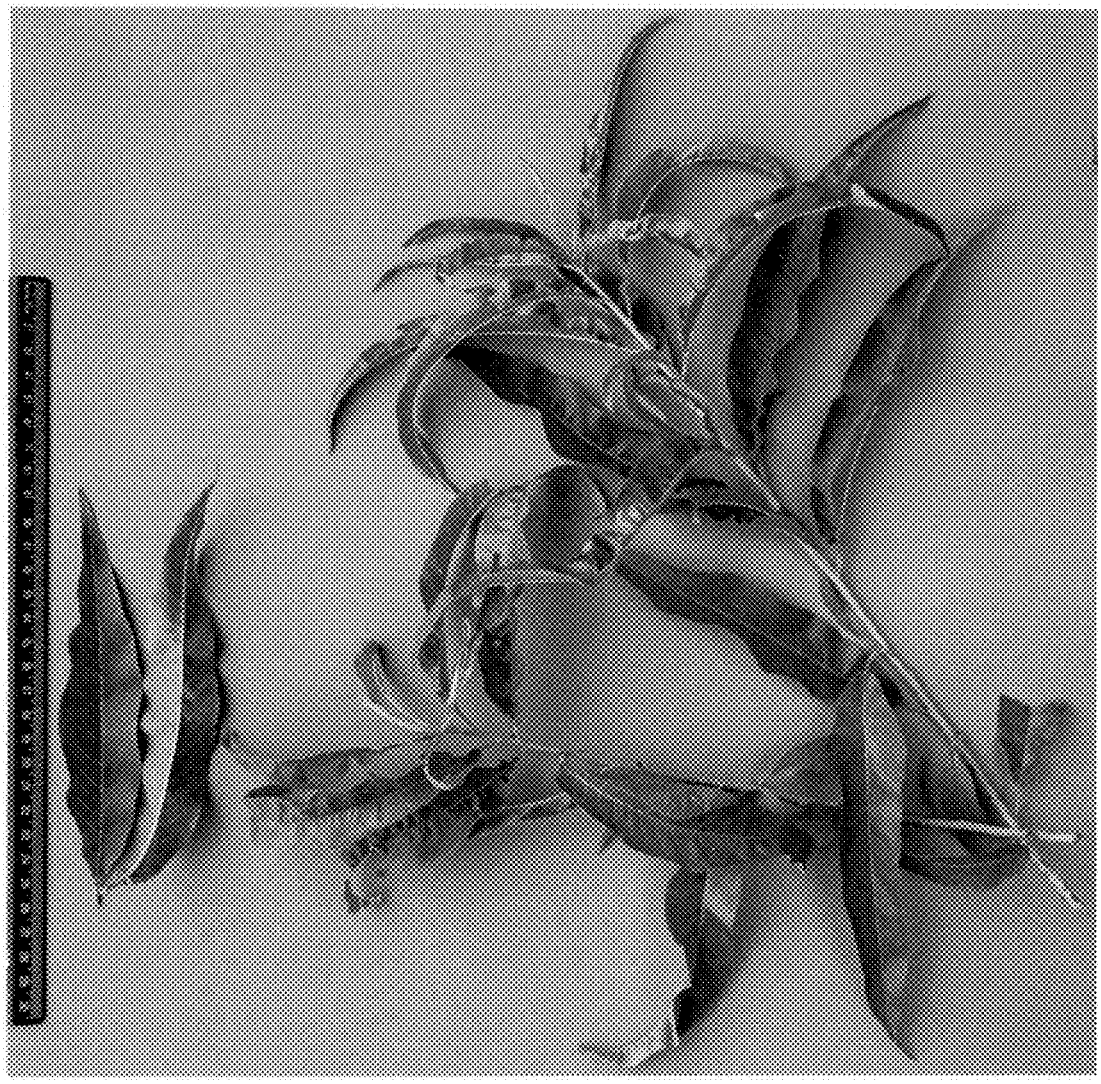
FIG. 4. A stem showing the leaves of 'TRH3C114W' peach. The ruler is in centimeters.
Figure 5:
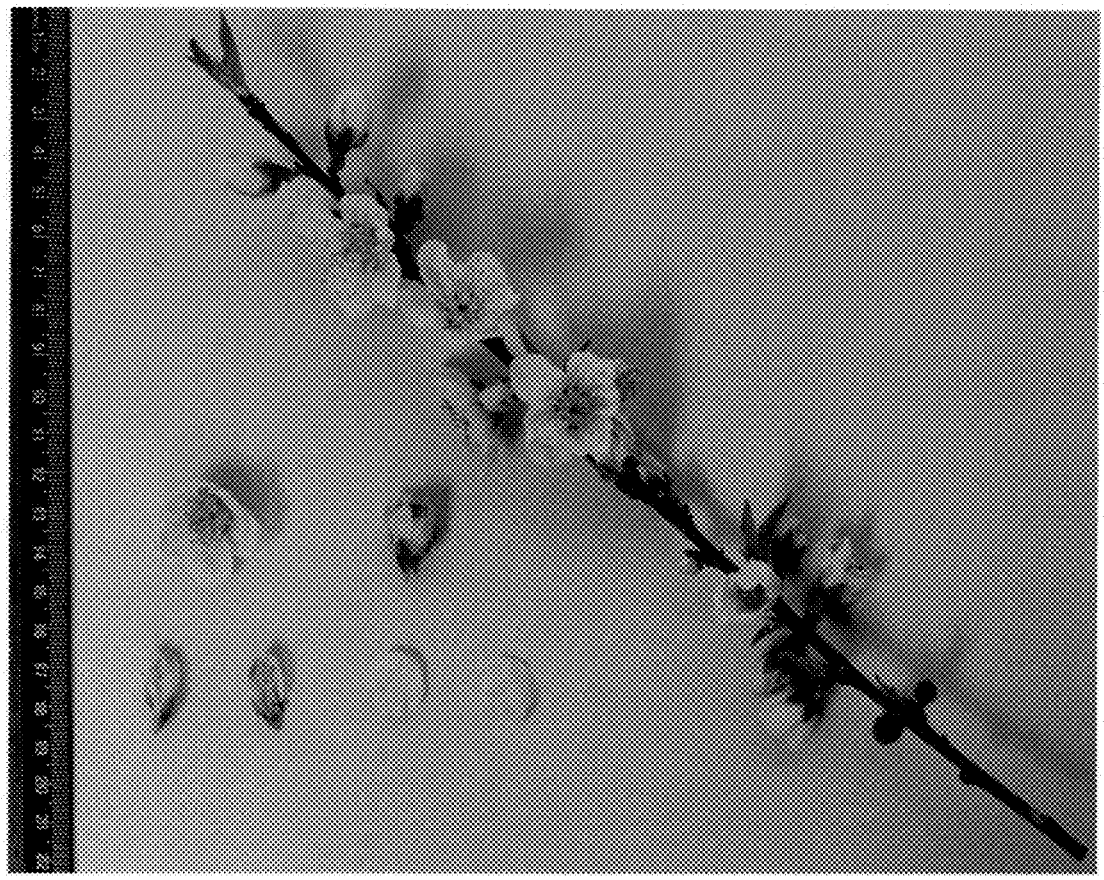
FIG. 5. A stem showing the flowers of 'TRH3C114W' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to The R.H.S. Colour Chart (2001 Edition) or The R.H.S. Mini Colour Chart (2005) provided by The Royal Horticultural Society of Great Britain. Colors are approximate as color depends on horticultural practices such as light level and fertilization rate, among others.

Tree:

*Size*.—Generally average as compared to other common peach cultivars ripening in the medium chill zone of Texas.

*Height*.—7 feet (2.1 m) at the end of the 2024 growing season.

*Width*.—7 feet width (2.1 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fruit cultivars for a full crop is one fruit every 6-8" of one-year old fruiting wood. Trees often set more fruit than needed for a full crop.

*Shape*.—The 'TRH3C114W' peach has been trained in an open center configuration but exhibits a semi spreading growth type as seen in peach varieties 'Texprince' (Byrne, D. H. and T. A. Bacon. 2004. TexPrince, a mid season medium chill peach. HortScience 39 (3):631-632; U.S. Plant Pat. No. 14,629, 23 Mar. 2004) and 'Texking' (Byrne, D. H. and T. A. Bacon. 2004. TexKing, an early ripening medium chill peach. HortScience 39:442-443, U.S. Plant Pat. No. 14,627, 23 Mar. 2004).

*Current season growth*.—The current season growth for the new variety was approximately 1 to 2 feet (0.3-0.61 m). Vigor is medium to medium low compared to other common peach varieties grown in the medium chill zone of Texas. Regularity of Bearing — Regular in the absence of temperatures of 28° F. or lower during bloom and considered hardy under typical conditions of the medium-chill zone of Texas.

Trunk:

*Size*.—Approximately 3 inches (7.6 cm) in diameter and 9.75 inches (24.8 cm) in circumference when measured at a distance of approximately 12 inches (30.5 cm) above the soil level, at the end of the 2024 growing season on a five-year old tree.

*Bark texture*.—Considered moderately rough with numerous folds of papery scarf-like skin being present. Bark Coloration — Variable, colors (RHS2001) present are 156D of the Green-White Group, 198A, 198B, 198C, 198D of the Greyed-Green Group and N200D of the Brown Group.

Branches:

*Size*.—Considered medium to moderately large for the species.

*Thickness*.—Average (about 3.5-5 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 5 to 6 mm in width and were approximately 1.5 to 2 mm in height. Density of lenticels was 1.0 lenticel per square centimeter.

*Current season shoots*.—Surface texture — Substantially glabrous.

*Internode length*.—Approximately 10 to 17 mm as measured in the middle of a current season stem. Color of Mature Branches — The predominant colors (RHS2001) are 156D of the Greyed-White Group, 166A, 175A and 176A of the Greyed-Orange Group, 178A of the Greyed-Red Group, N200D of the Brown Group and 201D of the Grey Group.

Leaves:

*Size*.—Considered medium to moderately large for the species. Leaf measurements have been taken from vigorous upright current season growth approximately at mid-shoot.

*Leaf length*.—Approximately 150 to 180 mm.

*Leaf width*.—Approximately 32 to 35 mm.

*Leaf thickness*.—Approximately less than 1 mm.

*Leaf form*.—Lanceolate.

*Leaf tip form*.—Acuminate.

*Leaf upper surface color* (*RHS*2001).—Green varying among 137A, 137B, and 137C of the Green Group and 146A of the Yellow-Green Group.

*Leaf lower surface color* (*RHS*2001).—Green varying among 137B, and 137C of the Green Group and 146A, and 146B of the Yellow-Green Group.

*Leaf lower mid-vein color* (*RHS*2001).—Light green, 145C and 145D of the Yellow-Green Group.

*Leaf margins*.—Form — Considered crenate. Uniformity — Considered generally uniform.

*Leaf petioles*.—Length — Approximately 10 to 12 mm. Thickness — Approximately 2 mm. Color (RHS2001) — Pale green, 144B, N144C, N144D, 145A and 145B of the Yellow-Green Group.

*Leaf glands*.—Size — Approximately 1-2 mm in height and 1 mm in width. Number — Generally 2-4 per leaf. Type — Reniform. Color (RHS2001) — Brown, 165A and 166A of the Greyed-Orange Group and N199B and N199C of the Grey-Brown Group.

*Leaf stipules*.—Length — Approximately 11 to 16 mm. Form — Lanceolate. Color (RHS2001) — Green, 144A, 144B, N144C, N144D, 145A, 145B and 146D of the Yellow-Green Group. Color is similar on both surfaces. The stipules are early deciduous. Ratio of wood (leaf) buds to flowering buds — 2 flower buds per vegetative bud.

Flowers:

*Floral buds*.—General — The floral buds are conic in form, and slightly appressed relative to the bearing shoot. Color — Mature buds are brown, (approximately 165A, 166B and 177A of the Greyed-Orange Group, 199B of the Grey-Brown Group and 200D of the Brown Group). The buds are considered hardy in the medium chill zone of Texas. Mature Bud Length — 4 to 5 mm. Mature Bud Width — Approximately 1 mm.

*Blooming type*.—Mean date of full bloom in the medium chill zone of Texas was in mid-February (February 14th at Somerville and February 12th at Fairfield experimental plot), a few days to one week before the commercial cultivars 'Texking' and 'Flordaking' (not patented, Andrews, 1979. 'Flordaking' peach. HortScience 14(1):81-82.).

*Flower type*.—Showy.

*Flower size*.—Flower diameter at full bloom is approximately 30 to 32 mm.

*Bloom quantity*.—Considered abundant.

*Flower bud frequency*.—Normally 2 per node.

*Petal size*.—Width — Approximately 12 to 13 mm. Length — Approximately 18 to 19 mm.

*Petal form*.—Broadly ovate.

*Petal count*.—Nearly always 5.

*Petal color* (*RHS*2001) *abaxial/adaxial*.—Light to medium pink when young (62B, 62C, 62D, 65B, 65C, 65D, 69A, 69B, 69C and 73C of the Red-Purple Group), becoming darker near the petal claw.

*Petal claw*.—Form — The claw is considered truncate in shape. Length — Approximately 1 mm. Width — Approximately 1 mm.

*Petal margins*.—Generally considered variable, from nearly smooth to slightly undulate.

*Petal apex*.—Generally — The petal apices appear round.

*Flower pedicel*.—Length — Average length of approximately 2 to 3 mm. Thickness — Approximately 1 to 2 mm. Color (RHS2001) — A light green (144D, N144A, N144C, 145A and 145B of the Yellow-Green Group).

*Floral nectaries*.—Color (RHS2001) — Light to medium yellow (2C, 3B, 3C, 4A, 4B, 7D, 8A, 9B, 9C and 9D of the Yellow Group).

*Sepals*.—Sepal number — 5 sepals per flower. Surface Texture — The surface has a short, fine, wooly texture. Size — Height 4.9 mm, Width 5.0 mm. Form — Ovate. Color (RHS2001) Abaxial — Maroon and green with white (approximately RHS2001 58A, 59A, 59B, 60A, 60B and 71A of the Red-Purple Group; 144B, 144C, N144A, N144C, 145A and 145B of the Yellow-Green Group and 155A, 155B, 155C and 155D of the White Group).

*Nectar cup* (*hypanthium*).—Surface Texture — Generally glabrous. Color (RHS2001) — Maroon with green (approximately 58A, 59A, 59B, 60A, 60B and 71A of the Red-Purple Group and 144B, 144C, N144A, N144C, 145A and 145B of the Yellow-Green Group).

*Anthers*.—Color (RHS2001) — Dark red (approximately 34A of the Orange-Red Group and 42A, 43A, 44A, 45A, 45B, 46A and 46B of the Red Group). Pollen Production — Pollen is abundant and is light to medium yellow in color (RHS2001) (approximately 2B, 2C, 3C, 3D, 4B and 4C of the Yellow Group). Filaments — Size — Variable in length, approximately 9 to 16 mm, with the filaments being shorter than the height of the pistil and petals. Color (RHS2001) — White (approximately 155A, 155B, 155C and 155D of the White Group) and darkening with advanced maturity.

*Pistil*.—General — Generally taller than the anther height and shorter than the petal height in the flower. Length — Approximately 19 to 21 mm, including the ovary. Color (RHS2001) — Considered white to light yellow when young (approximately 1B, 1C, 1D of the Green-Yellow Group and 155A, 155B, 155C and 155D of the White Group) and becoming slightly darker with advancing senescence. Surface Texture — The variety has a pubescent style and ovary.

Fruit:

*Maturity when described*.—The present variety of fruit is described, as it would be found in its firm ripe condition at full commercial maturity. Under the ecological conditions prevailing in the medium chill zone of Texas it would be ripe in mid-to late May. The average ripe date was May 18$^{th}$, May 28$^{th}$, and May 25$^{th}$ at Pleasanton, Somerville, and Fairfield respectively.

*Size*.—General — Medium large to large for the season and considered uniform. Average Cheek Diameter — Approximately 60 to 68 mm. Average Suture Diameter — Approximately 59 to 67 mm. Average Axial Diameter — Approximately 46 to 59 mm.

*Fruit form*.—Generally considered round. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Dark pink to maroon, 46A 47A, 53A and 53B of the Red Group, 59A, 59B and 60A of the Red-Purple Group and 183A, 183B, 183C, 184A, 184B, 185A, N186C, 187A and 187B of the Greyed-Purple Group.

*Ventral surface*.—Form — Considered uniform.

*Stem cavity*.—Width — Approximately 14 to 17 mm. Length — Approximately 21 to 23 mm. Depth — Approximately 9 to 11 mm.

*Fruit base*.—Flat.

*Fruit apex*.—Flat.

*Fruit stem*.—Length — 8 to 10 mm. Thickness — Approximately 2 to 3 mm. Color (RHS2001) — Medium brown, 166A, 175A, 176A, 177A, 178A and 178B of the Greyed-Orange Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — No cracking observed. Skin Color — Generally — Variable. A medium to very large amount (approximately 70-95%) of the fruit surface covered with a dark pink to maroon blush. Blush Color (RHS2001) — Dark pink to maroon. Mainly, 39A, 39B, 45D, 46D, 47D, 50B and 53A of the Red Group, 59A, 59B and 60A of the Red-Purple Group and 185A, 185B, N186C, 187A and 187B of the Greyed-Purple Group. Skin Ground Color (RHS2001) — Pale to medium yellow. 1D of the Green-Yellow Group, 2D, 4C, 4D, 5D, 6D, 8C, 8D, 9D, 10C, 10D, 11B, 11C, 12D and 13D of the Yellow Group, 12D of the Yellow-Orange Group and 160B of the Greyed-Yellow Group.

*Flesh color* (*RHS*2001).—White with maroon. 46A of the Red Group, 58A, 59B, 59C, 60A and 60B of the Red-Purple Group and 187C of the Greyed-Purple Group.

*Flesh fibers*.—Present, numerous and lightly colored. These fibers are present throughout the flesh.

*Stone cavity color* (*RHS*2001).—White to greenish white. 1D of the Green-Yellow Group, 155A, 155B, 155C and 155D of the White Group and 158A and 158B of the Yellow-White Group.

*Flesh texture*.—Generally, the flesh is considered firm at commercial maturity.

*Ripening*.—Generally the fruit of the present variety ripens evenly.

*Flavor*.—Considered sweet (12 Brix) with an acidic flavor.

Stone:

*Attachment*.—Clingstone at commercial maturity.

*Stone size*.—Generally considered small to medium relative to the ratio of stone to fruit size. Length — Approximately 22 to 30 mm. Width — Approximately 18 to 21 mm. Thickness — Approximately 14 to 16 mm.

*Fibers*.—Generally, very few medium length fibers are attached sporadically along the surface of the stone.

*Stone form*.—Rounded to elliptical.

*Apex base angle*.—Medium.

*Stone shape*.—Variable, rounded to ovoid.

*Stone surface*.—Surface Texture — Consists of single pits, rosettes of pits and chains of pits. Ridges — Numerous fine ridges are present basally and converge towards the base of the stone.

*Ventral edge*.—Medium.

*Dorsal edge*.—Shape — Grooved and having moderately rough edges.

*Stone color* (*RHS*2001).—The color of the dry stone is medium tan, 165C, 165D and 168D of the Greyed-Orange Group. The color of the inside surface of the endocarp is primarily light tan, 158A of the Yellow-White Group, 159A and 159B of the Orange-White Group and 164D of the of the Greyed-Orange Group.

*Tendency to split*.—Splitting is relatively uncommon.

*Kernel*.—The kernel fills the endocarp at harvest. When dried the shriveled kernels measure approximately 3 mm in thickness, 7-8 mm in width, and 11-15 mm in length. The colors (RHS2001) of the shriveled kernels are variable from medium brown to tan. 163A, 163C, 164B, 164C, 164D, 165B, 165C, 165D, 166C and 167B of the Greyed-Orange Group.

*Use*.—The subject variety, 'TRH3C114W', is a peach tree of early maturity, which produces white-fleshed, sweet-acidic, clingstone to semi-freestone fruit which are firm, with a 70-95% dark pink to maroon blush over a light yellow ground color and are useful for the fresh fruit market.

*Keeping quality*.—Average. Retains firmness and flavor after 14 days of refrigeration at 3-5° C.

*Resistance to insects and disease*.—Moderately susceptible to bacterial leaf spot (*Xanthomonas campestris* cv. *pruni*) as is the variety 'Texking'. Otherwise, no atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH3C114W', as illustrated and described herein.

* * * * *